United States Patent [19]

Wolf et al.

[11] Patent Number: 5,462,874
[45] Date of Patent: Oct. 31, 1995

[54] DIALYZED MULTIPLE WELL TISSUE CULTURE PLATE

[76] Inventors: Martin L. Wolf, 1280 Keston St., St. Paul, Minn. 55108; John R. Wilson, 173 Windsor La., New Brighton, Minn. 55112

[21] Appl. No.: 81,541

[22] Filed: Jun. 23, 1993

[51] Int. Cl.[6] ............................................. C12M 3/00
[52] U.S. Cl. ................... 435/297.5; 435/305.2; 435/305.3; 422/101; 422/102; 436/178
[58] Field of Search ........................... 422/99, 101, 102; 435/283–287, 293, 296–301; 436/178, 807, 809

[56] References Cited

U.S. PATENT DOCUMENTS

| | | | |
|---|---|---|---|
| 2,677,646 | 5/1954 | Lovell et al. | 435/297 X |
| 2,761,813 | 9/1956 | Goetz | 435/301 X |
| 4,012,288 | 3/1977 | Lyman et al. | 435/284 |
| 4,125,436 | 11/1978 | Liner | 435/287 |
| 4,246,339 | 1/1981 | Cole et al. | 422/102 X |
| 4,308,351 | 12/1981 | Leighton et al. | 435/284 |
| 4,670,396 | 6/1987 | Bear et al. | 435/310 X |
| 4,797,259 | 1/1989 | Matkovich et al. | 422/101 |
| 4,871,674 | 10/1989 | Matsui et al. | 435/284 |
| 4,963,490 | 10/1990 | Churchouse et al. | 435/284 X |
| 5,026,649 | 6/1991 | Lyman et al. | 435/297 X |
| 5,139,951 | 8/1992 | Butz et al. | 435/297 X |
| 5,141,718 | 8/1992 | Clark | 435/285 X |
| 5,366,893 | 11/1994 | Stevens et al. | 435/284 |

OTHER PUBLICATIONS

Schweitzer, Handbook of Separation Techniques for Chemical Engineers, pp. 2–5 and Feb. 24–Feb. 26, 1979.
Hawley, The Condensed Chemical Dictionary, 10th edition, p. 650, 1981.

Primary Examiner—James C. Housel
Assistant Examiner—Maureen M. Wallenhorst
Attorney, Agent, or Firm—Sprung Horn Kramer & Woods

[57] ABSTRACT

A multiple well tissue culture plate (10) having a plurality of opened bottomed wells (36) with a semi-permeable membrane (20) across the bottoms of a plurality of such wells (36). The multiple well tissue culture plate (10) is placed in contact with the basal medium (26) contained within the basal medium reservoir (12) to allow for exchange of nutrients and waste products between the basal medium (26) and the culture medium (22) across the semi-permeable membrane (20). The dialyzed multiple well tissue culture plate (50) provides dialysis of each individual well within the multiple well tissue culture plate (10) thus eliminating traditional exchange of culture medium to maintain proper culture conditions.

6 Claims, 4 Drawing Sheets

DIALYZED MULTIPLE WELL TISSUE CULTURE PLATE

BACKGROUND—FIELD OF THE INVENTION

This invention relates to a device for growing cells or tissue in vitro.

BACKGROUND—DESCRIPTION OF PRIOR ART

Conventional multiple well tissue culture plates as invented by Liner (U.S. Pat. No. 3,597,326) and Lyman (U.S. Pat. No. 4,012,288) are a common tool in most tissue culture experiments requiring small numbers of cells in relatively small volumes under multiple experimental conditions. The Terisaki tissue culture plate (U.S. Pat. No. 4,599,315)) is used mainly in experiments aimed at cloning cells. Among the advantages of multiple well tissue culture plates are their low cost, disposable nature, and multiplicity of cell culture compartments. Multiple well tissue culture plates make possible multiple separate cultures all within a single culture device, thus making them attractive in screening monoclonal anitbody producing cells, examination of biological effects of growth factors, large screenings of cell clones, and for cultures in which small numbers of cells are available. Multiple well tissue culture plates are available in standard configurations, having 6, 12, 24, 48 or 96 wells per plate, which allow users to select a plate which has the desired well volume most suitable for a specific application. Plates with many wells, such as 48 or 96 well plates, are a good tool for use in experiments with many variables or experiments with a small number of cells. Plates with fewer numbers of wells that are larger in size are typically used in lieu of numerous separate cell culture flasks. It is the ability to handle a complete cell culture experiment with multiple parameters in an individual plate that makes these devices a common tool in most tissue culture experiments.

Multiple well tissue culture plates are comprised of a number of wells which are generally cylindrical in nature with a closed bottom upon which the cells reside. Closed bottom tissue culture devices such as tissue culture flasks and petri dishes are common to research laboratories. All closed bottom devices have common means for supporting cells. Oxygenation of the cells occurs as oxygen diffuses into the culture medium from the ambient gas residing above the culture medium. Maintaining appropriate levels of nutrients and waste products in the culture medium is accomplished by periodically removing a volume of culture medium and replacing this volume with fresh culture medium. Cultures grown with this type of protocol are commonly referred to as static cultures, and multiple well tissue culture plates fall into the static culture genre of culture devices.

Although it is clear that the multiple well tissue culture plate is an advantageous tool for use in tissue culture experimentation, the closed bottom nature of the wells and resultant static culture protocol limits experimental design and experimental results. Specifically, the need to periodically remove and add culture medium to the wells creates limitations.

There have been several patents issued with regard to the multiple well tissue culture plate, but no inventions to date have changed the static nature of the device. Improvements to the device have focused on problems that arise from static culture protocols, but have not eliminated the need for removal and replacement of culture medium. Instead, improvements have focused on symptoms of the problem.

For example, removing the multiple well tissue culture plate from the humidified incubator in which it resides during operation and placing it under a laminar flow hood to access the culture medium can result in evaporation of the small volume of culture medium residing within individual wells. Guhl et al. (U.S. Pat. No. 4,657,867) devised a cover which minimizes evaporation by structurally controlling the distance between the top cover and the multiple well tissue culture plate. Removing the cover from the multiple well tissue culture plate to access the culture medium increases the possibility of contamination. Lyman (U.S. Pat. No. 4,495,289) teaches of a hinged cover which minimizes the number of wells exposed to air borne contaminants. The amount of time that the wells are exposed when the cover is removed during culture medium exchange is proportional to the risk of both evaporation and contamination. Several manufacturers sell a manifolded pipet which can access twelve wells simultaneously. The use of this type of pipet minimizes the time in which the multiple well tissue culture plate cover is removed and thus minimizes the risk of evaporation and contamination.

Ancillary apparatus, referred to as "Transwells" (Co-Star, Oxnard, Calif.), are used to extend the applications of the multiple well tissue culture plate are on the market. These are devices (U.S. Pat. No. 5,026,649 and U.S. Pat. No. 5,139,951 ) which are used in combination with multiple well tissue culture plates to provide more in-vivo like growth environments. These devices are intended to provide a permeable growth surface which is removable from the well and are sold as individual units which must be inserted into each individual well of a multiple well tissue culture plate. In operation, neither of these devices reduces the need for feeding, provide concentrated product, minimize contamination and evaporation or allow one to culture cells at high densities. Furthermore, the use of these devices to separate two cell populations so as to study the influences of soluble factors on each population is not optimal as the concentration of these soluble factors is constantly diluted with feedings. Although these devices utilize a permeable membrane to provide an improved in vitro culture environment, they still require culture medium exchange during operation and therefore do not address the problems that are the direct result of this procedure.

A detailed description of the limitations inherent to the modern day multiple well tissue culture plate will be beneficial in understanding the source of these problems.

In Vitro Cell Densities: Wells of the tissue culture plate may hold small volumes of fluid in which the cells reside. This small volume in the well is advantageous when multiple experimental manipulations are desired so that addition of exogenous factors such as antibodies, cytokines, or DNA to numerous wells does not require large amounts of these factors. However, with the small volumes and normal tissue culture cell densities, the numbers of cells which are exposed to these factors is limited. Therefore, subsequent analysis of the impact of added factors on the cells in culture usually is limited by the number of cells which can be recovered for analysis. An improved device which allows higher cell densities will address this limitation.

Cloning Experiments: Cloning experiments in which cells are being screened or selected following deposition of multiple individual clones per well are limited. When rapidly dividing cells coexist in the same well with slowly dividing cells, the rate of culture medium exchange is dictated by the metabolic activity of the rapidly dividing cells. As the frequency of required culture medium exchange becomes unmanageable, cells are deliberately removed from the well to slow the process. If the secreted product of the clones is of interest as in the isolation of positive clones during hybridoma fusion and screening, the need to remove cells due to rapid outgrowth may lead to false negative values for wells in which a positive clone is under represented in the population. Furthermore, the concentration of the secreted product being screened will be continually diluted by the exchange of culture medium. In these applications an improved multiple well tissue culture plate that eliminates the current medium exchange protocol is desirable.

Medium Conditioning Effect: The ability to study cell biology of cells in-vitro, cultured in a fashion most similar to that found within the organism in which cells are taken from, is a goal for modern cell biologists. Thus, the ability to culture cells at higher densities than in normal static tissue culture and with concentrated conditioning effects on the culture medium by the cells would be desirable. The multiple well tissue culture plate does not allow for these attributes and thus improvements to the device would make it more desirable for cell biology studies.

Exogenous factors: Exogenous factors such as antibodies, cytokines, or DNA are often expensive. As culture medium exchange takes place to control the level of nutrients and waste products within the wells, these factors are removed and must be replaced resulting in increased use of these expensive factors. A multiple well tissue culture plate that does not require accessing individual wells to maintain appropriate levels of metabolites and which uses exogenous factors more efficiently would be desirable.

Cell Disturbances: Exchange of the culture medium within each well of the multiple well tissue culture plate is conducted by using a pipet for removal and addition of medium. In cultures in which an adherent cell monolayer is growing on the bottom of the well, care must be used during culture medium exchange such that pipette tips must be carefully manipulated so that the adherent monolayer is not disturbed or destroyed. Some cell monolayers will detach completely from the bottom of the well in response to a very limited disruption due to disturbance from a pipette tip. Therefore, an enhanced multiple well tissue culture plate with reduced need to insert pipetes into the well is desirable.

Variance In Culture Medium Composition Between Wells: In experiments in which various metabolic rates are present in different cell populations residing within individual wells, the influence of altered pH, lactic acid, depleted glucose or amino acids may add to experimental variation between wells. Often, the culture medium of a multiple well tissue culture plate is exchanged every time the well with the greatest metabolic activity requires culture medium exchange. Thus, wells in which little metabolic activity occurs are often fed simply because other metabolically active wells within the same plate need culture medium exchange. This leads to inequalities with regards to conditioning effects by the cells in each well. A multiple well tissue culture plate which would maintain equal concentrations of nutrients and metabolic byproducts such as lactic acid, as well as maintain equal pH in each well during culture would allow for more equivalency between culture conditions in each well and thus be a more rigorous experimental device for cell biology.

Contamination Risk: Repeated handling of multiple well tissue culture plates during extended cultures increases the risk of contamination. Additionally, feeding each well by pipette is usually conducted such that a common pipette tip is used to feed more than one well. This leads to increased risk of contamination of wells due to the spreading of a contaminant from one well to other wells via the pipette tip. This often results in loss of many experimental data points as numerous wells become contaminated. Furthermore, if the pipette tip is used to feed several multiple well tissue culture plates, cross contamination between entire plates becomes possible. Thus, the medium exchange procedure of the multiple well tissue culture plate leads to possible loss of experimental data or cells due to contamination risks. A multiple well tissue culture plate which eliminates the need to directly access the wells of the multiple well tissue culture plate for culture medium exchange would clearly be at less risk of inadvertent contamination.

Evaporative Effects: The evaporative loss of fluid from the wells of multiple well tissue culture plates can be so noticeable that visible changes in volumes within the wells after exposure to less than 100% humidified atmosphere can be seen. Therefore, removal of the multiple well tissue culture plate from the incubator leads to evaporative losses. During culture medium exchange the volume is replaced, however with time an increase in solute concentration will occur as a result of the evaporative loss of water from the culture medium. This leads to altered osmotic conditions in the culture well which will tend to accumulate over the duration of the culture. A multiple well tissue culture plate which minimizes the increase of solute concentration due to evaporative loss of water is desirable.

Labor intensive: Many experiments in multiple well tissue culture plates require elaborate experimental matrixes to examine the impact of various biological factors at different doses and in different combinations on the biology of the cells in an experiment. If the experiment is to continue for a duration in which culture medium exchange must occur, than the effort expended to establish appropriate biological conditions when the experiment was initially set up must be repeated again during culture medium exchange to insure the experimental matrix remains unaltered. This task can become very labor intensive and prone to mistakes. Therefore, a multiple well tissue culture plate which reduces the need to exchange culture medium within the wells will also reduce the labor involved in repeatedly establishing the original experimental conditions in the well during medium exchange.

Small Culture Volumes: Each well of a standard ninety-six well tissue culture plate will typically hold 100–200 microliters of culture medium volume. In cloning experiments such as those conducted in Terasaki tissue culture plates, the culture medium volume of each well is typically 10 microliters. The reduced well volume magnifies all of the problems described above. Thus, a multiple well tissue culture plate that addressee the limitations described previously would be beneficial in cloning experiments and other experiments using very small culture medium volumes.

OBJECTS

It is the aim of the invention to provide an improved multiple well tissue culture plate that addresses the problems previously discussed. Prior inventions aimed at improving the multiple well tissue culture plate have been directed at peripheral modifications to minimize limitations caused by traditional, static culture medium exchange. We have sought to eliminate the need to directly access the individual wells in order to maintain an appropriate cell growth climate.

It is clear that the current methods of removing and replacing culture medium leads to limited cell exposure to exogenous factors, uncertainty in cloning experiments, physical cell disturbance, well to well variance in culture medium composition, contamination risk, evaporation effects, excess labor, and experimental limitations when small volumes are needed. While the multiple well tissue culture plate remains a simple and useful experimental tool, addressing the cause of the aforementioned shortcomings will significantly enhance its usefulness. If an improved multiple well tissue culture plate which addresses the above mentioned limitations and is still inexpensive, simple to use and disposable then this improved multiple well tissue culture plate will aid researchers in their work.

BRIEF SUMMARY OF THE INVENTION

In accordance with the invention there is provided an improved multiple well tissue culture plate;
 a. that eliminates the need to access each well individually for culture medium exchange.
 b. that allows for the culture of cells at increased cell densities not achievable in current static cell culture procedures.
 c. which allows for increased concentration of cell secreted products.
 d. which makes more efficient use of expensive growth and other exogenous factors.
 e. that is more representative of in vivo conditions.
 f. which reduces the physical disturbance of cells in culture.
 g. that minimizes well to well variance in pH, lactic acid, glucose concentrations, amino acids, and other variables that are dictated by the metabolic activity of the cells present within the wells.
 h. that reduces the risk of contamination to the cell culture by eliminating the need to directly access the wells during culture medium exchange.
 i. that reduces the amount of evaporative loss from the culture fluid by eliminating the need to periodically remove the multiple well tissue culture plate from humidified surroundings in order to directly access the wells during culture medium exchange.
 j. that requires less labor throughout the course of the culture.
 k. which allows for culturing cells in very small volumes that are less subject to problems normally associated with very small culture volumes.
 l. that does not limit the concentration of soluble biological factors secreted by cells within the wells and can be used in conjunction with a current products designed for use in multiple well tissue culture plates to study relationships between different cell types.

BRIEF DESCRIPTION OF THE DRAWINGS

Still further objects and advantages will become apparent from a consideration of the ensuing description and drawings wherein.

Figure 1:
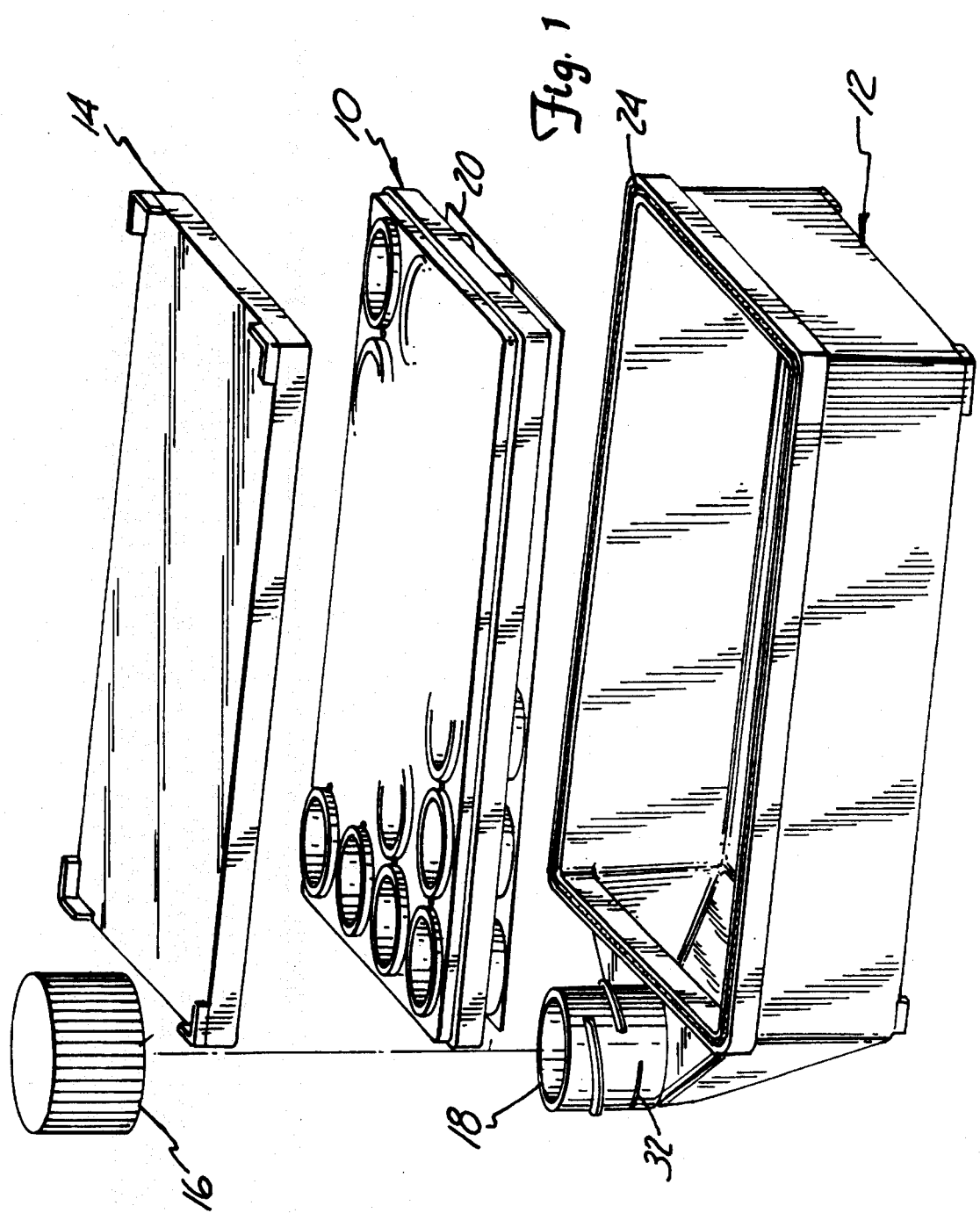
FIG. 1 is an exploded view of a typical 24 well embodiment of the dialyzed multiple well tissue culture plate.

Reference Numerals In Drawings 10 multiple well tissue culture plate
12 basal medium reservoir
14 top cover
16 basal medium access port cap
18 basal medium access port
20 semi-permeable membrane
22 culture medium
24 gasket seal
26 basal medium
28 bottom cover
30 individual compartment
32 fluid fill line
34 well wall
36 well
38 feet
40 stacking locator
44 gasket seat
46 multiple well tissue culture plate seating guide
50 dialyzed multiple well tissue culture plate

DESCRIPTION–FIGS. 1 TO 5

FIG. 1. A typical embodiment of a dialyzed multiple well tissue culture plate 50 is illustrated in FIG. 1. A multiple well tissue culture plate 10 resides within a basal medium reservoir 12. A top cover 14 resides on top of multiple well tissue culture plate 10. A basal medium access port cap 16 covers a basal medium access port 18 to basal medium reservoir 12. A fluid fill line 32 is indicated on basal medium access port 18. A semi-permeable membrane 20 is fastened to the bottom of multiple well tissue culture plate 10.

Figure 2:
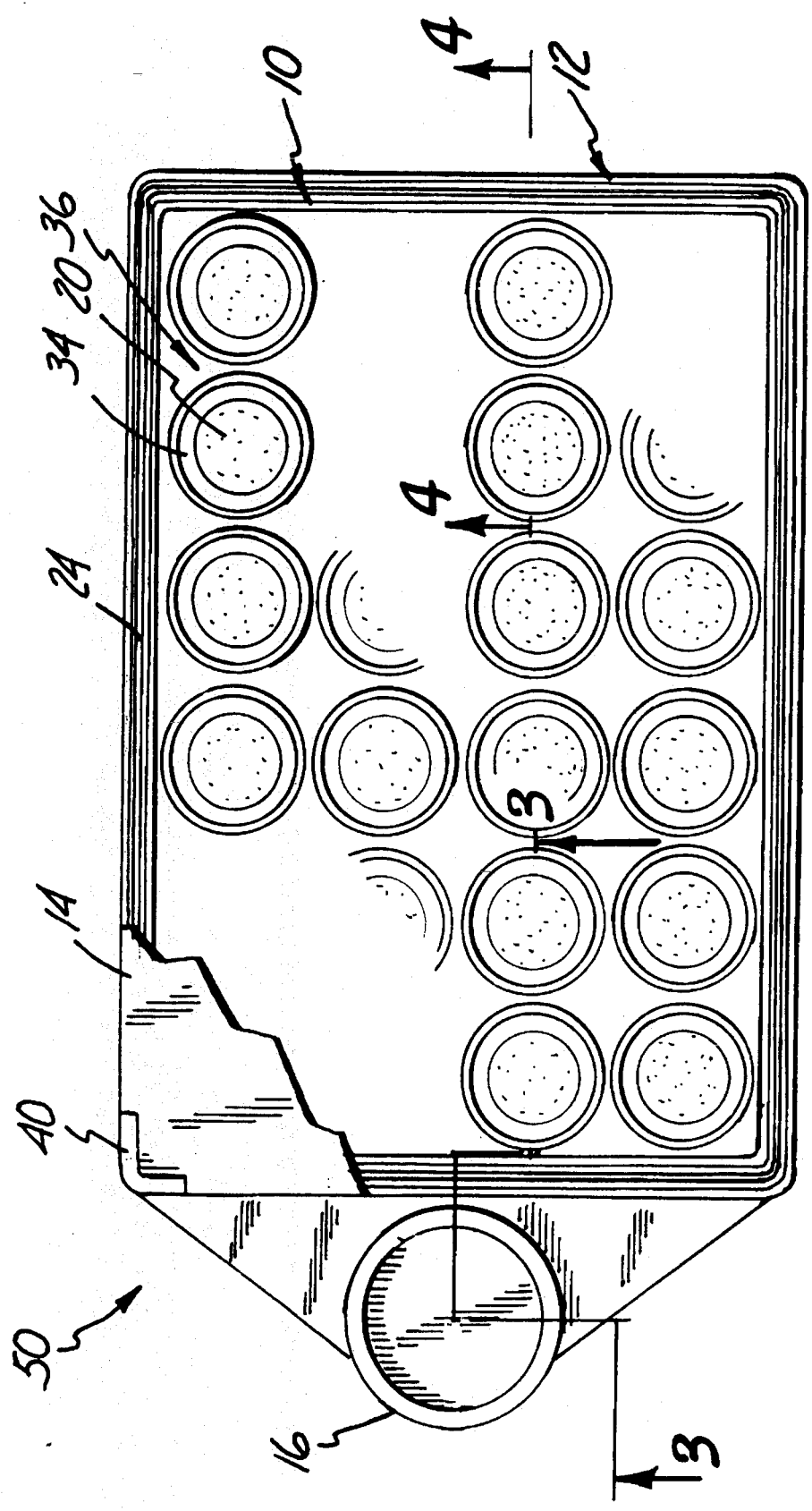
FIG. 2 is a top view of the embodiment shown in FIG. 1.

FIG 2. FIG. 2 shows a top view of the embodiment shown in FIG. 1. Semi-permeable membrane 20 is shown comprising the bottom of each well 36. Top cover 14 is shown with a stacking locator 40. A basal medium access port cap 16 is shown in place on basal medium reservoir 12.

Figure 3:
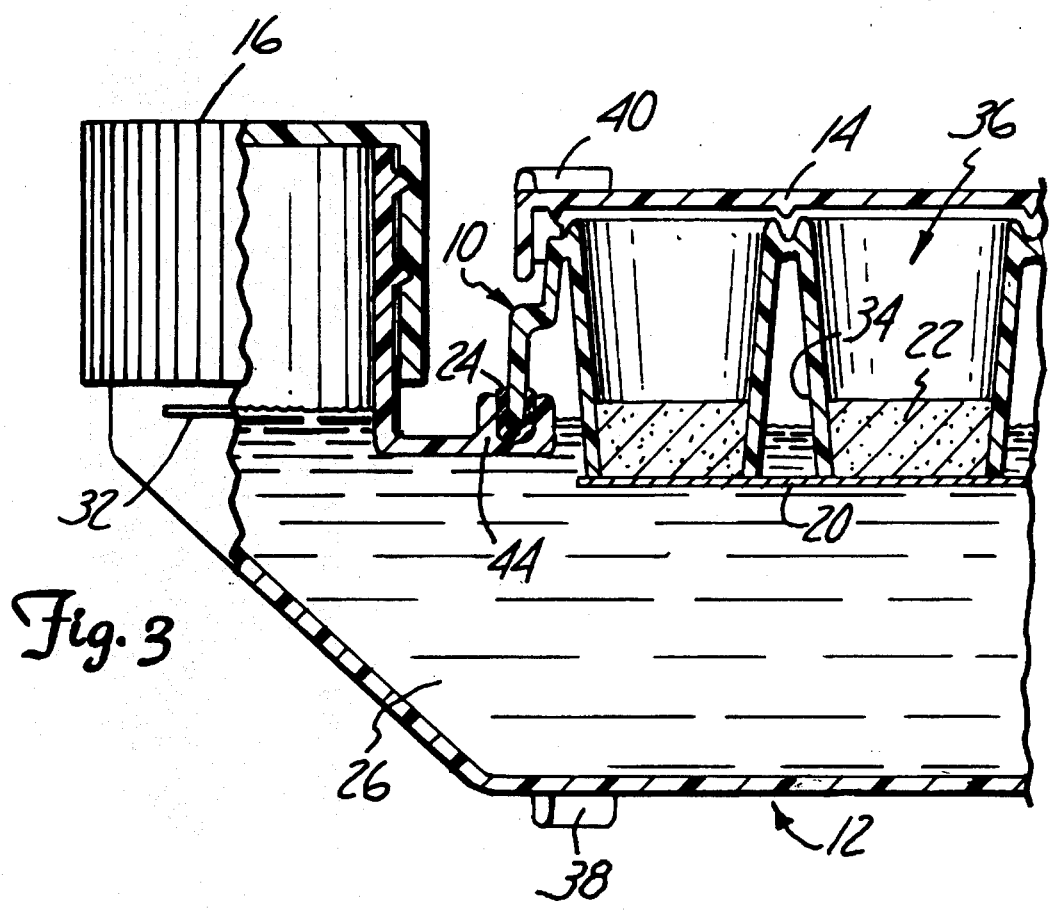
FIG. 3 is a cross-sectional view through the embodiment shown in FIG. 2 taken along section line 3—3.

FIG. 3. Cross section 2—2 of the embodiment of FIG. 2 is shown in FIG. 3. In dialyzed multiple well tissue culture plate 50, multiple well tissue culture plate 10 has a bottom comprised of semi-permeable membrane 20. A culture medium 22 is shown in well 36 comprised of a vertical well wall 34 and bottom semi-permeable membrane 20. Removable top cover 14 resides on top of multiple well tissue culture plate 10. A gasket seal 24 resides in a gasket seat 44 providing a liquid tight seal between multiple well tissue culture plate 10 and basal medium reservoir 12. A basal medium 26 fills basal medium reservoir 12 such that semi-permeable membrane 20 is submerged. Fluid fill line 32 provides a sight gauge to show the proper fill level of basal medium 26 during operation. Feet 38 mate with stacking locator 40 on top cover 14 to allow dialyzed multiple well tissue culture plate 50 to be stacked upon itself.

Figure 4:
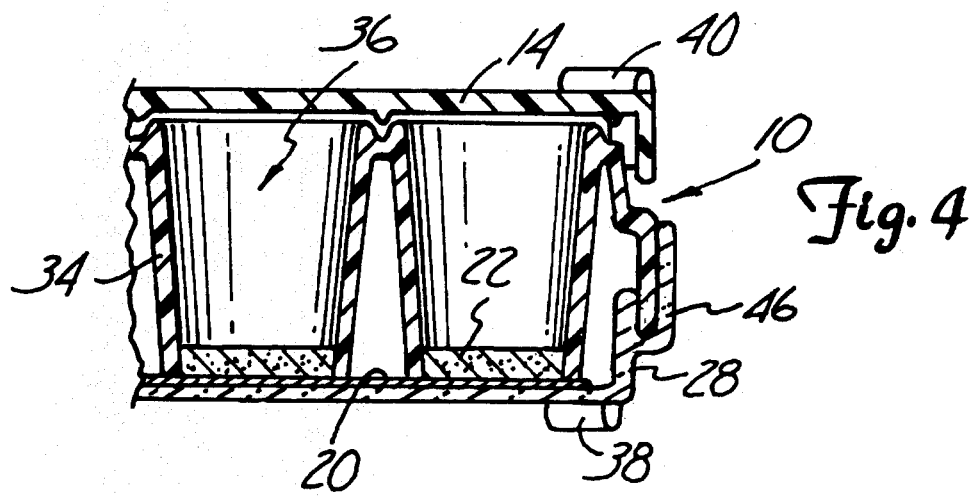
FIG. 4 is a cross section of the multiple well tissue culture plate through section line 4—4 of FIG. 2 and inserted into a bottom viewing cover.

FIG. 4. FIG. 4 shows a cross sectional view of multiple well tissue culture plate 10 attached to bottom cover 28. In this embodiment, semi-permeable membrane 20 rests directly upon a bottom cover 28. Feet 38 on bottom cover 28 mate with stacking locator 40 on top cover 14. A multiple well tissue culture plate seating guide 46 provides the interface between multiple well tissue culture plate 10 and bottom cover 28.

Figure 5:
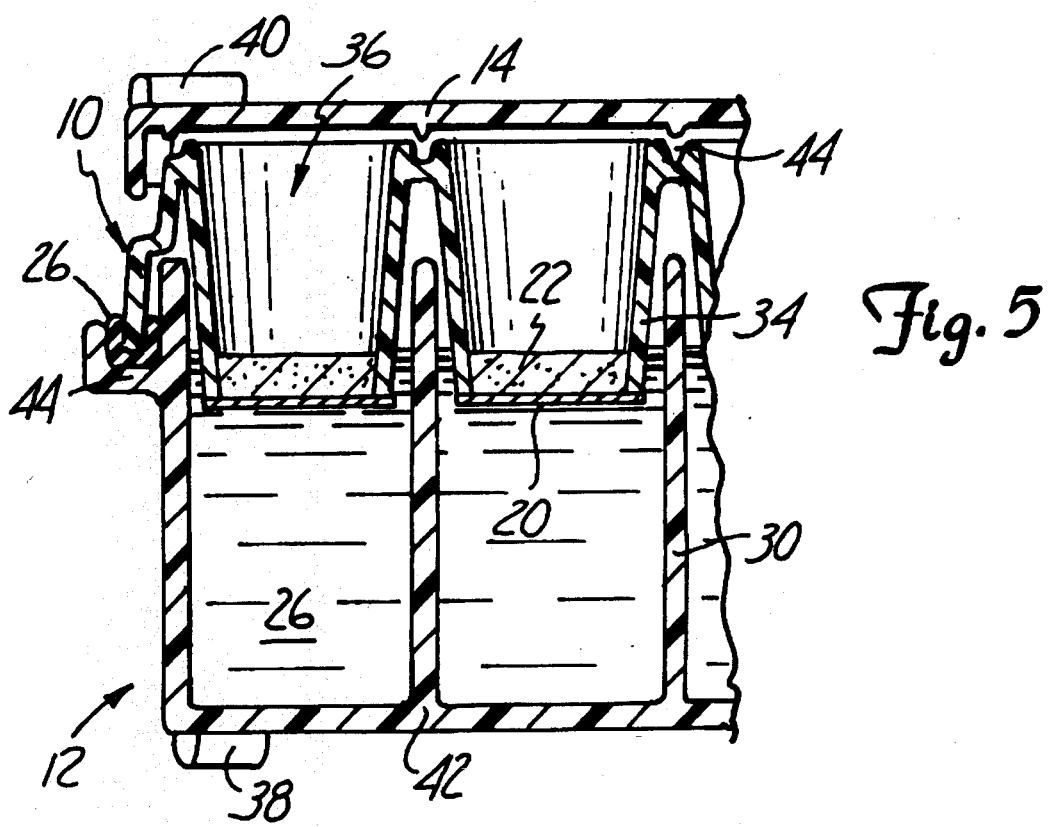
FIG. 5 is a cross section showing two wells of an additional embodiment in which each well is partially submerged within an individual medium reservoir.

FIG. 5. FIG. 5 is a cross-sectional view of an additional embodiment showing wells 36 of multiple well tissue culture plate 10. Dialyzed multiple well tissue culture plate 50 is configured such that each well 36 is partially submerged within an individual compartment 30 of basal medium reservoir 12. Gasket 24 allows for a liquid tight seal between multiple well tissue culture plate 10 and basal medium reservoir 12. Feet 38 on basal medium reservoir 12 mate with stacking location 40 on top cover 14.

Operation of Dialyzed Multiple Well Tissue Culture Plate

Culture medium 22 is in communication with basal medium 26 across semi-permeable membrane 20 as shown in the preferred embodiment detailed in FIG. 3.. Maintenance of an appropriate environment for cell growth is the result of diffusion of waste products from culture medium 22 into basal medium 26. In a similar fashion, nutrients diffuse into culture medium 22 from basal medium 26. The driving force for mass transfer is the result of concentration differences of diffusible molecules between culture medium 22 and basal medium 26 across semi-permeable membrane 20. These differences arise from cell consumption of nutrients and cell production of wastes. The pore size of semi-permeable membrane 20 dictates the size of molecules which can pass through semi-permeable membrane 20. Small molecular species such as glucose and lactate diffuse freely through the pores. The size of molecules which are excluded from the pore, and thus incapable of traversing through the membrane, is determined by the molecular weight cutoff properties of semi-permeable membrane 20. In this fashion, the choice of pore size of semi-permeable membrane 20 will dictate the molecular composition of culture medium 22.

Delivery and removal of the gases oxygen and carbon dioxide relics upon the development of concentration differences between the partial pressures of the gas in culture medium 22 and the partial pressures of the gas in the ambient environment. For example, as oxygen is consumed by cells within culture medium 22, a gradient develops between culture medium 22 and the ambient atmosphere in which the apparatus resides. Gas molecules travel passively between the cell space and the ambient atmosphere via a tortuous path between top cover 14 and multiple well tissue culture plate 10. Net movement of oxygen is thus from the area of higher concentration in the ambient atmosphere to the area of low concentration in culture medium 22 and thus to the cells. In a similar fashion, carbon dioxide produced in culture medium 22, travels into the ambient environment and is reduced in culture medium 22. Dialyzed multiple well tissue culture plate 50 utilizes the above described principles to provide and remove gas for culture.

The manner of using the dialyzed multiple well tissue culture plate is now described. To provide dialysis of each well 36 of multiple well tissue culture plate 10, one must fill basal medium reservoir 12 with basal medium 26 to a level which coincides with fluid fill line 32. This is accomplished by removing basal medium access cap 16 and either pouring or pipetting basal medium 26 into basal medium reservoir 12 through basal medium access port 18. Typically, basal medium reservoir 12 is capable of holding twenty five times the combined individual well culture medium 22 volumes. The selection of basal medium reservoir 12 volume will be determined by the application in which the apparatus is used. For primary cultures of untransformed cells in which large numbers of cells are not an issue, a smaller basal medium reservoir 12 would be adequate. In contrast, for applications in which large numbers of cells or increased metabolic activity is present a larger basal medium reservoir 12 would be desireable. The use of a different sized basal medium reservoir 12 allows the investigator to select appropriate volumes for individual experiments and thus not waste medium or be constrained by the need to replace basal medium too frequently.

Basal medium 26 is typically stored at 4° C. As it rises in temperature to equilibrate with the ambient conditions of the tissue culture incubator, it will expand in volume. To prevent the volume expansion from creating a potentially damaging pressure increase in basal medium reservoir 12, basal medium reservoir cap 16 is loosened during temperature equilibration to create a vent which allows basal medium 26 to expand into the excess capacity of basal medium access port 18.

Air bubbles which may accumulate after filling can be removed by tilting basal medium reservoir 12 appropriately to allow bubbles to accumulate within the neck of basal medium access port 18. After filling basal medium reservoir 12, basal medium access port cap 16 is tightly screwed down on basal medium access port 18 liar ease of handling. Multiple well tissue plate 10 is now ready for inoculation with tissue samples or cells.

Inoculation of cells requires removing top cover 14 to expose multiple well tissue culture plate 10. Cells can be delivered by pipette through the top opening of each individual well 36 suspended in a given volume of culture medium 22. Alternatively, culture medium 22 can be added without cells into each well 36, and cells can then be added in an additional small volume of culture medium 22. The set up of culture medium 22 and cells in the dialyzed multiple well tissue culture plate 50 is identical to that for a traditional static culture multiple well tissue culture plate. Replacement of top cover 14 is followed by slightly loosening basal medium access port cap 16 and placing dialyzed multiple well tissue culture plate 50 into a standard tissue culture incubator.

During culture basal medium 26 will accumulate metabolic waste products and become depleted of metabolic substrates as cells within the well 36 consume substrates and produce waste products. Basal medium 26 can be removed from basal medium reservoir 12 by removing basal medium access port cap 16 and removing basal medium 26 through basal medium access port 18 by aspiration or pipetting. The need to change basal medium 26 can be determined by either visually inspecting the color of basal medium 26 if a pH indicator is present, which is common, or by quantitative analysis of either lactic acid or glucose concentrations. When a desired set point in lactic acid or glucose concentration is achieved, basal medium 26 can be replaced. Replacement of basal medium 26 may either comprise complete removal and replacement, or removal of a fraction of basal medium 26 and replacement with fresh basal medium 26.

No manipulation of culture medium 22 is required during operation to maintain appropriate conditions for cell growth. However, depending upon the cell type which is in culture medium 22, the need for removal of cells at various time points may be required. As the cell mass increases within well 36, the maximum number of viable cells which can be supported within well 36 is approached as diffusion through the cell mass becomes limited Thus, to maintain a majority of viable cells within well 36, biomass will need to be reduced on occasion. This is best determined for each cell type cultured. In our experience, if rapidly proliferating cells are not removed from well 36, the number of viable cells will reach a maximum value and remain constant, while nonviable cells continue to accrue, and with time viable cells will become a smaller percentage of total cell mass within well 36. This occurs primarily in cultures of rapidly growing cells once the available supportive space within the well is occupied. After this has occurred, any further increase in cell numbers necessarily leads to increased numbers of cells which can not be maintained in a viable state.

Operational Considerations

The operation of dialyzed multiple well tissue culture plate 50 as described above is straight forward. However, to permit dialysis and ease of operation several considerations need to be addressed in the structure of dialyzed multiple well tissue culture plate 50. To assure proper dialysis semi-permeable membrane 20 must be completely submerged in basal medium 26. To assure that culture conditions of each individual well 36 within multiple well tissue culture plate 10 is equivalent, so as to allow quantitative analysis of cells grown in the dialyzed multiple well tissue culture plate 50, several parameters must be addressed. And finally, the properties of semi-permeable membrane 20 impact the operation and performance of dialyzed multiple well tissue culture plate 50. These considerations are described next.

In theory, basal medium 26 must only be in contact with semi-permeable membrane 20 for functional operation. In practice, there are factors which must be considered to insure this condition is met. Excess volume capacity, typically ranging from 5% to 15% of basal medium reservoir 12 volume, is designed into basal medium access port 18. This excess capacity allows a portion of basal medium 26 to reside above the level of semi-permeable membrane 20 when basal medium 26 is pipetted or poured to fluid fill line 32 of basal medium reservoir 12. Further volume which resides above semi-permeable membrane 20 is present on the outside of each individual well 36, placing additional basal medium 26 volume above the level of the semi-permeable membrane 20. Typically, ten to twenty milliliters of basal medium 26 will reside five to ten millimeters above semi-permeable membrane 20. This volume of basal medium 26 which resides above the level of semi-permeable membrane 20 provides hydraulic force to keep basal medium 26 in contact with the underside of semi-permeable membrane 20. The volume of basal medium 26 residing above semi-permeable membrane 20 insures that the underside of semi-permeable membrane 20 is in complete communication with basal medium 26.

The excess capacity designed into basal medium reservoir 12 is also available to collect gas released from basal medium 26. As basal medium 26 rises in temperature when dialyzed multiple well tissue culture plate 50 is placed in a standard incubator, the gas carrying capacity of basal medium 26 is reduced. This results in the formation of gas bubbles within basal medium reservoir 12. If bubbles become trapped under semi-permeable membrane 20, effective dialysis of culture medium 22 becomes limited. Therefore, the excess volume contained in basal medium access port 18 acts as an accumulator for this gas. In operation, the user will manipulate dialyzed multiple well tissue culture plate 50 so as to remove bubbles in contact with semi-permeable membrane 20 and cause the bubbles to relocate to basal medium access port 18, which is the highest point in basal medium reservoir 12.

It is desireable for each well 36 of dialyzed multiple well tissue culture plate 512) to present identical physical conditions for cell culture. One factor which could lead to well to well variability is a different volume of culture medium 22 between any well 36. The ability to maintain equivalent culture medium 22 volumes in each well 36 is dependent upon the careful addition of equal volumes of fluid at the start of the experiment. In traditional multiple well tissue culture plates, culture medium variation between wells can result from two sources. First, inconsistency between wells can occur when adding culture medium at the beginning of an experiment or when performing culture medium exchange during the coarse of an experiment. Second, evaporation of culture medium from the wells during the experiment can cause well to well variations.

In dialyzed multiple well tissue culture plate 50 the traditional sources of culture medium variation are considered in addition to that caused by membrane flux. First, variations resulting from culture medium 22 addition are possible, although in this case there is a clear improvement relative to traditional multiple well tissue culture plates as the culture medium is not exchanged by direct access of well 36, but instead is dialyzed by basal medium 26. Therefore, the number of times a mistake can be made is minimized as set up occurs only once during the culture.

Second, evaporation frequently occurs in conventional multiple well tissue culture plates leading to variations in culture medium volumes between wells. Normal manipulations of these culture plates results in appreciable evaporative losses of liquid from wells. This effect can be significant, and its impact is greatest on wells which reside on the perimeter of the plate. Current practice in some laboratories is to not use these perimeter individual wells and to instead fill them with distilled water. Most evaporative losses occur when the tissue culture plate is removed from the incubator and the top cover is removed in a laminar flow air hood for culture medium exchange.

Dialyzed multiple well tissue culture plate 50 does not require direct accesss to well 36 to maintain proper growth conditions in culture medium 22. Instead, basal medium 26 is replaced when it has been depleted in nutrients such as glucose and has absorbed waste products such as lactate. Due to quantitiy of basal medium 26 relative to culture medium 22, basal medium 26 exchange occurs less frequently than traditional culture medium exchange due to the large capacity of basal medium 26 to deliver nutrients to and absorb waste from culture medium 22. Thus, dialyzed multiple well tissue culture plate 50 is not removed from the humidified incubator as frequently as traditional multiple well tissue culture plates, nor is the top cover removed as frequently.

Third, liquid flux across semi-permeable membrane 20 could lead to changes in culture medium 22 volume, thus causing either an increase or decrease from the volume which the researcher initially established within well 36 by adding cells and medium. Therefore, careful consideration of hydraulic flux across semi-permeable membrane 20 is critical to this aspect of exprimental consistency.

The liquid flux across semi-permeable membrane 20 is a function of hydraulic pressure differential, membrane pore size, and osmotic pressure differential. Liquid movement between culture medium 22 and basal medium reservoir 12 across semi-permeable membrane 20 will occur more readily when semi-permeable membrane 20 contains large pores. In most instances, semi-permeable membranes which have pore sizes that allow molecules between 10,000 and 50,000 daltons to pass are insensitive to the small hydraulic pressure difference between the culture medium 22 and basal medium reservoir 12. Therefore, the typical five to ten millimeter head height of basal medium 26 relative to culture medium 22 head height will have no significant consequence on the volume of culture medium 22 when semi-permeable membrane 20 contains pore sizes which exclude molecules greater than 50,000 daltons in size. Although water molecules are 18 daltons, they do not traverse semi-permeable membrane 20 at the hydraulic pressures which are present in dialyzed multiple well tissue culture plate 50. The capillary forces within the pores of the membrane act to retain water within the pore and thus provide resistance to fluid flux across the membrane.

The hydraulic flux characteristics of a membrane are not only determined by the size of the pore within the membrane, but also by the chemical nature of the membrane. A hydrophillic membrane such as polyacrylonitrile will be more wettable than a hydrophobic membrane such as polytetrafluoroethylene and thus more capable of higher flux at equivalent pressure differential and surface area. Although this factor is a design consideration, the use of hydrophillic membranes at the typical pressure differential between basal medium 26 and culture medium 22 will not lead to significant volume variation in well 36.

Osmotic pressure differentials across semi-permeable membrane 20 will be determined by osmotically active substances present on both sides of the membrane. The pore size of semi-permeable membrane 20 will determine which solutes are osmotically active, thus proteins residing in culture medium 22 that exceed the molecular weight cutoff properties of semi-permeable membrane 20 will generally be the osmotically active molecules because they cannot traverse semi-permeable membrane 20. In practice, osmotic forces exert little if any significant effect on liquid movement in or out of culture medium 22. This may be due to the small numbers of osmotically active molecules in culture medium 22 relative to basal medium 26. If osmotic forces become an issue during unique experiments, they can be manipulated by addition of equal amounts of exogenous protein, such as serum supplements, to both culture medium 22 and basal medium 26. Therefore, liquid flux due to osmotic pressure differential across semi-permeable membrane 20 can be prevented.

In traditional multiple well tissue culture plates the loss of water through evaporation leads to an increase in solute concentration. This occurs because the lost water volume is generally replaced by the researcher with medium, and therefore the concentration of even small molecular weight solutes continues to rise throughout the culture. This problem is addressed in dialyzed multiple well tissue culture plate 50. Specifically, as the solute concentration rises in well 36 due to evaporation, a concentration gradient is established across semi-permeable membrane 20. Solutes will travel from well 36 to basal medium 26 until equilibrium is reached. Therefore, the well 36 solute concentration is more stable than that of traditional multiple well tisssue culture plate use.

The surface characteristics of the area upon which cells reside in culture will influence the numbers of cells which can be supported in each well. Cells in culture medium 22 are influenced by gravity. Cells which normally do not adhere to plastic are grown in what is termed suspension culture. However, in culture, these cells settle out of suspension readily and accumulate on the bottom of culture vessel. This is a concern as the bottom of well 36 is comprised of semi-permeable membrane 20. The material characteristics of the membrane can influence the shape the membrane takes when it becomes wet and thus a sagging or wrinkling shape can cause an excessive amount of cells to accumulate in the low portions of the membrane. Certain semi-permeable membrane compositions will swell when wet. Traditional cellulose based dialysis membranes tend to swell appreciably when wetted. This swelling leads to wrinkling when the membrane is fixed to the bottom of a cylindrical well. Pockets of cells will accumulate on the wrinkles within semi permeable membrane 20 and may reach cell densities in which anoxic conditions exist and diminished viability results. The number of viable cells which can be supported on a flat membrane will exceed the number which can be supported on a wrinkled membrane. Small wrinkles and low spots result in accumulation of cells in these areas and no cell mass on the high spots. This further limits the number of viable cells which can be supported within each well as the entire surface of semi permeable membrane 20 is not utilized.

Certain membranes are more suited to use as semi-permeable membrane 20 than traditional cellulose based membranes. These membranes arc not normally associated with passive dialysis but rather are used in pressure driven ultrafiltration applications. These are thin skinned membranes composed of polyacrylonitrile, polysulfone, or polyftetrafluoroethylene polymers which have been cast on the top of a dimensionally stable matrix such as polyolefin or polypropylene. These membranes provide flat growth surfaces on the bottom of culture medium 22 as the dimensionally stable matrix prevents sagging or wrinkling of the membrane. These semi-permeable membranes thus optimize cell growth within well 36 and are uniquely suited for this application.

Solid phase chemical interactions between molecules in solution and semi-permeable membrane 20 are also taken into consideration when selecting appropriate semi-permeable membranes. Thus one can exploit the surface characteristics of a membrane to either enhance or reduce cellular interactions with the membrane. A membrane which will bind protein and thus may lead to cell adhesion can be selected for applications in which cell attachment to semi-permeable membrane is desired. Conversely, membranes with low protein binding characteristics will tend to resist cell attachment and may be employed when cell attachment is not desired. These membrane selections are included in additional embodiments of the dialyzed multiple well tissue culture plate 50.

Additional Embodiments and Features

The dialyzed multiple well tissue culture plate 50 may present itself in a number of embodiments. The means in which the multiple well tissue culture plate 10 is attached to basal medium reservoir 12 can be in a removable or a permanently fixed fashion. The basal medium reservoir 12 can provide batch dialysis of multiple well tissue culture plate 10 or may be configured to dialyze each well 36 separately. These additional configurations are now discussed In the embodiment shown in FIG. 3, semi-permeable membrane 20 is secured to the bottom of each well 36 of multiple well tissue culture plate 10 such that the entire bottom circumference of well 36 is sealed to semi-permeable membrane 20. Methods of sealing include adhesive bonding, heat sealing, ultrasonic welding, and gasket compression seals The best sealing method will vary depending on the exact material composition of semi-permeable membrane 20 and multiple well tissue culture plate 10. In embodiments with numerous small wells, a sheet of membrane may be used to individually seal each well and thus avoid the need to die cut small membrane pieces and attach each one individually. The embodiments shown in the figures employ adhesives to seal semi-permeable membrane 20 to each well 36. The embodiments shown are not meant to restrict the means for attaching semi-permeable membrane 20 to well 36.

The embodiment in FIG. 3 shows the cross-sectional view taken along section 3—3 of FIG. 2. In this embodiment multiple well tissue culture plate 10 is shown secured to basal medium reservoir 12 by gasket seal 24. Gasket seal 24, seated within gasket seat 44, allows for removal and insertion of multiple well tissue culture plate 10 from basal medium reservoir 12. When multiple well tissue culture plate 10 is seated in gasket 24, a liquid tight seal is provided. This makes handling of dialyzed multiple well tissue culture plate 50 more convenient as fluid within basal medium reservoir 12 can only pass through basal medium access port 18. Thus, handling of dialyzed multiple well tissue culture plate 50 will not lead to fluid spills. The use of gasket seal 24 to seal multiple well tissue culture plate 10 to basal medium reservoir 12 as shown in FIG. 3 need not limit other embodiments wherein multiple well tissue culture plate 10 is secured by other liquid tight sealing means that allows dissassembly and reassembly to basal medium reservoir 12. Other embodiments may employ self sealing adhesives or flexible flanges to provide a liquid tight seal. Dialyzed multiple well tissue culture plate 50 may be embodied in such fashion that multiple well tissue culture plate 10 is sealed to basal medium reservoir 12 with adhesive or heat welding for applications in which removal of multiple well tissue culture plate 10 from basal medium reservoir 12 is not required. Allowing multiple well tissue culture plate 10 to float on basal medium 26 is yet another embodiment. The use of a sealing means to seat multiple well tissue culture plate 10 to basal medium reservoir 12 is beneficial in the following embodiments.

In FIG. 3 basal medium reservoir 12 need not be of a disposable nature. Polysulfone, or other autoclavable plastic will allow basal medium reservoir 12 to be reused. This reuseable basal medium reservoir 12 embodiment minimizes environmental waste and expense to the user as only multiple well tissue culture plate 10 need be disposed of.

Gasket seal 24 also allows multiple well tissue culture plate 10 to be attached to bottom cover 28 as shown in FIG. 4. In this configuration multiple well tissue culture plate 10 can be transported conveniently with semi-permeable membrane 20 protected and supported When multiple well tissue culture plate 10 is inserted into bottom cover 28 the device becomes analogous to a conventional multiple well tissue culture plate such that one may now use assessment instruments such as proliferation assay equipment, microscopes and the like. Not only does this configuration provide for easy transportation, but it also creates a profile which is acceptable for proper interface with these instruments. Therefore, with rigid bottom cover 28 attached, multiple well tissue culture plate 10 is analogous to traditional multiple well tissue culture plates and critical features of the standard dimensional format are retained.

An additional embodiment shown in FIG. 5 provides individual basal medium reservoirs 12 for each well of multiple well tissue culture plate 10. This embodiment is beneficial when there is a concern regarding batch dialysis of all wells in multiple well tissue culture plate 10. In this embodiment, each well 36 has its own basal medium reservoir 12 in which semi-permeable membrane 20 is kept submerged in basal medium 26. This embodiment is useful when semipermeable membrane 20 has a large pore size that could allow biologically active molecules to diffuse across semi-permeable membrane 20 and influence neighboring wells. In this embodiment each well is dialyzed by an individual basal medium reservoir 12. The filling of these individual reservoirs will require more effort from the investigator as each reservoir compartment will need to be filled individually. The geometry of the basal medium reservoir 12 and individual well 36 of multiple well tissue culture plate 10 assures the contact of basal medium 26 with semipermeable membrane 20 to allow for dialysis. This embodiment provides the researcher with further flexibility in experimental protocol and expands the applications in which dialyzed multiple well tissue culture plate 50 would be desirable.

Traditional multiple well tissue culture plates have undergone minimal functional improvement since multiple well tissue culture plate was invented by Liner and Lyman. In spite of this, the multiple well tissue culture plate is embraced by researchers and employed in numerous applications. The features of the disclosed dialyzed multiple well tissue culture plate offer several clear improvements over traditional multiple well tissue culture plates. The improvements resulting from our dialyzed multiple well tissue culture plate are:

increased concentration of cell secreted products increased cell densities more in-vivo like growth conditions more efficient use of exogenous factors reduced cell disturbance over the course of a culture reduced well to well variation in culture medium metabolite concentrations reduced contamination risk reduced evaporation of the culture medium reduced labor increased ability to perform cultures in very small volumes Although the description above contains many specifications, these should not be construed as limiting the scope of the invention but merely providing illustrations of some of the presently preferred embodiments of this invention.

We claim:

1. A multiple well tissue culture assembly comprising a) a plate comprising a plurality of wells each open at the top and bottom and defining a first predetermined volume, b) a membrane closing off the bottom of each well, said membrane excluding passage therethrough of molecules in excess of a predetermined size between 10,000 and 50,000 daltons, c) a common reservoir defining a second predetermined volume greater than the sum of the first predetermined volumes of a plurality of said wells, said common reservoir having an access port for adding basal medium to and removing basal medium from said reservoir, and d) means for securing said plate to said reservoir so that when said reservoir contains a basal medium, said medium is in contact with the membrane which closes the bottoms of the wells.

2. An assembly according to claim 1, wherein the membrane closing off the bottom of each well is part of a common semi-permeable membrane.

3. An assembly according to claim 2, further including a bottom cover for covering the membrane closing off the bottoms of each of said wells, and means for removably connecting said bottom cover to said plate, whereby said plate can be removed from said reservoir and the bottom cover connected thereto for inspection or transport of the contents of the wells of said plate.

4. An assembly according to claim 1, further comprising at least one additional common reservoir, whereby said plate and membrane closing off the bottoms of each of said wells on said plate can be secured sequentially to either reservoir.

5. An assembly according to claim 1, further comprising a bottom cover for covering the membrane closing off the bottoms of each of said wells, and means for removably connecting said bottom cover to said plate, whereby said plate can be removed from said reservoir and the bottom cover connected thereto for inspection or transport of the contents of the wells of said plate.

6. An assembly according to claim 1, wherein said reservoir includes vertical means subdividing it into at least two separate sub-reservoirs, whereby the membrane below some of said wells contacts medium in one of said at least two sub-reservoirs and the membrane below other of said wells contacts medium in another of said at least two sub-reservoirs.

* * * * *